(12) United States Patent
Deransart et al.

(10) Patent No.: US 12,740,873 B2
(45) Date of Patent: Sep. 22, 2026

(54) SHOULDER PATIENT SPECIFIC INSTRUMENT

(71) Applicant: Tornier SAS, Saint Martin (FR)

(72) Inventors: Pierric Deransart, Saint Martin d'uriage (FR); Emmanuel Francois Marie Lizee, Saint Ismier (FR); Delphine Claire Michelle Henry, Saint Ismier (FR); Jean Chaoui, Locmaria-Plouzane (FR); Gilles Walch, Lyons (FR); Pascal Boileau, Nice (FR)

(73) Assignee: TORNIER SAS (FR)

( * ) Notice: Subject to any disclaimer, the term of this patent is extended or adjusted under 35 U.S.C. 154(b) by 224 days.

(21) Appl. No.: 18/504,276

(22) Filed: Nov. 8, 2023

(65) Prior Publication Data

US 2024/0091029 A1 Mar. 21, 2024

Related U.S. Application Data

(62) Division of application No. 17/451,499, filed on Oct. 20, 2021, now Pat. No. 12,097,129, which is a
(Continued)

(51) Int. Cl.
*A61F 2/46* (2006.01)
*A61B 17/17* (2006.01)
(Continued)

(52) U.S. Cl.
CPC ........ *A61F 2/4612* (2013.01); *A61B 17/1739* (2013.01); *A61B 17/1778* (2016.11);
(Continued)

(58) Field of Classification Search
CPC .... A61F 2/4612; A61F 2/4081; A61F 2/4603; A61F 2002/4677; A61B 17/1739; A61B 17/1778; A61B 2017/568
See application file for complete search history.

(56) References Cited

U.S. PATENT DOCUMENTS 4,919,670 A 4/1990 Dale et al.
5,030,219 A 7/1991 Matsen, III et al.
(Continued)

FOREIGN PATENT DOCUMENTS

AU 2021203700 B2 8/2023
CA 2927086 4/2015
(Continued)

OTHER PUBLICATIONS

US 9,451,972 B2, 09/2016, Lang et al. (withdrawn)
(Continued)

*Primary Examiner* — Sameh R Boles
(74) *Attorney, Agent, or Firm* — DUANE MORRIS LLP

(57) ABSTRACT

A system for guiding a glenoid prosthesis is disclosed. The system includes a glenoid guide that includes: a guide feature; at least three arms having a first end coupled with the guide feature and a second end disposed away from the guide feature; at least three peripheral pegs, each peripheral peg extending from the second end of a corresponding arm and includes an engagement surface configured to engage the scapula of the patient; and a strut extending laterally from the guide feature.

11 Claims, 5 Drawing Sheets

Related U.S. Application Data division of application No. 16/521,466, filed on Jul. 24, 2019, now Pat. No. 11,179,249, which is a division of application No. 15/024,747, filed as application No. PCT/IB2014/002711 on Nov. 11, 2014, now Pat. No. 10,405,993.

(60) Provisional application No. 61/903,814, filed on Nov. 13, 2013.

(51) Int. Cl.
*A61B 17/56* (2006.01)
*A61F 2/40* (2006.01)

(52) U.S. Cl.
CPC ....... *A61B 2017/568* (2013.01); *A61F 2/4081* (2013.01); *A61F 2/4603* (2013.01); *A61F 2002/4677* (2013.01)

(56) References Cited

U.S. PATENT DOCUMENTS

| | | | |
|---|---|---|---|
| 5,329,846 | A | 7/1994 | Bonutti |
| 5,370,692 | A | 12/1994 | Fink et al. |
| 5,383,938 | A | 1/1995 | Rohr et al. |
| 5,531,793 | A | 7/1996 | Kelman et al. |
| 5,610,966 | A | 3/1997 | Martell et al. |
| 5,725,586 | A | 3/1998 | Sommerich |
| 5,768,134 | A | 6/1998 | Swaelens et al. |
| 5,769,856 | A | 6/1998 | Dong et al. |
| 5,779,710 | A | 7/1998 | Matsen, III |
| 5,807,437 | A | 9/1998 | Sachs et al. |
| 5,824,078 | A | 10/1998 | Nelson et al. |
| 5,824,085 | A | 10/1998 | Sahay et al. |
| 6,002,859 | A | 12/1999 | DiGioia, III et al. |
| 6,129,764 | A | 10/2000 | Servidio |
| 6,155,812 | A | 12/2000 | Smith et al. |
| 6,172,856 | B1 | 1/2001 | Jang |
| 6,183,519 | B1 | 2/2001 | Bonnin et al. |
| 6,364,910 | B1 | 4/2002 | Shultz et al. |
| 6,385,475 | B1 | 5/2002 | Cinquin et al. |
| 6,432,142 | B1 | 8/2002 | Kamiya et al. |
| 6,459,948 | B1 | 10/2002 | Ateshian et al. |
| 6,648,894 | B2 | 11/2003 | Abdelgany et al. |
| 6,699,289 | B2 | 3/2004 | Iannotti et al. |
| 6,719,799 | B1 | 4/2004 | Kropf |
| 6,772,026 | B2 | 8/2004 | Bradbury et al. |
| 6,797,006 | B2 | 9/2004 | Hodorek |
| 6,915,150 | B2 | 7/2005 | Cinquin et al. |
| 6,944,518 | B2 | 9/2005 | Roose |
| 7,468,075 | B2 | 12/2008 | Lang et al. |
| 7,469,474 | B2 | 12/2008 | Farrar |
| 7,534,263 | B2 | 5/2009 | Burdulis, Jr. et al. |
| 7,542,791 | B2 | 6/2009 | Mire et al. |
| 7,599,539 | B2 | 10/2009 | Kunz et al. |
| 7,618,451 | B2 | 11/2009 | Berez et al. |
| 7,634,119 | B2 | 12/2009 | Tsougarakis et al. |
| 7,648,530 | B2 | 1/2010 | Habermeyer et al. |
| 7,717,956 | B2 | 5/2010 | Lang |
| 7,747,305 | B2 | 6/2010 | Dean et al. |
| 7,796,791 | B2 | 9/2010 | Tsougarakis et al. |
| 7,799,077 | B2 | 9/2010 | Lang et al. |
| 7,802,503 | B2 | 9/2010 | Couvillion et al. |
| 7,822,588 | B2 | 10/2010 | Mueller et al. |
| 7,831,079 | B2 | 11/2010 | Kunz et al. |
| 7,927,338 | B2 | 4/2011 | Laffargue et al. |
| 7,981,158 | B2 | 7/2011 | Fitz et al. |
| 7,983,777 | B2 | 7/2011 | Melton et al. |
| 8,007,448 | B2 | 8/2011 | Barrera |
| 8,014,984 | B2 | 9/2011 | Iannotti et al. |
| 8,055,487 | B2 | 11/2011 | James |
| 8,062,302 | B2 | 11/2011 | Lang et al. |
| 8,066,708 | B2 | 11/2011 | Lang et al. |
| 8,077,950 | B2 | 12/2011 | Tsougarakis et al. |
| 8,083,745 | B2 | 12/2011 | Lang et al. |
| 8,094,900 | B2 | 1/2012 | Steines et al. |
| 8,105,330 | B2 | 1/2012 | Fitz et al. |
| 8,122,582 | B2 | 2/2012 | Burdulis, Jr. et al. |
| 8,160,325 | B2 | 4/2012 | Zug et al. |
| 8,160,345 | B2 | 4/2012 | Pavlovskaia et al. |
| 8,175,683 | B2 | 5/2012 | Roose |
| 8,214,016 | B2 | 7/2012 | Lavallee et al. |
| 8,221,430 | B2 | 7/2012 | Park et al. |
| 8,231,634 | B2 | 7/2012 | Mahfouz et al. |
| 8,234,097 | B2 | 7/2012 | Steines et al. |
| 8,337,501 | B2 | 12/2012 | Fitz et al. |
| 8,337,503 | B2 | 12/2012 | Lian |
| 8,337,507 | B2 | 12/2012 | Lang et al. |
| 8,343,218 | B2 | 1/2013 | Lang et al. |
| 8,350,186 | B2 | 1/2013 | Jones et al. |
| 8,366,771 | B2 | 2/2013 | Burdulis, Jr. et al. |
| 8,377,073 | B2 | 2/2013 | Wasielewski |
| 8,377,129 | B2 | 2/2013 | Fitz et al. |
| 8,382,765 | B2 | 2/2013 | Axelson et al. |
| 8,439,926 | B2 | 5/2013 | Bojarski et al. |
| 8,444,651 | B2 | 5/2013 | Kunz et al. |
| 8,457,930 | B2 | 6/2013 | Schroeder |
| 8,460,304 | B2 | 6/2013 | Fitz et al. |
| 8,475,463 | B2 | 7/2013 | Lian |
| 8,480,753 | B2 | 7/2013 | Collazo et al. |
| 8,480,754 | B2 | 7/2013 | Bojarski et al. |
| 8,500,740 | B2 | 8/2013 | Bojarski et al. |
| 8,529,568 | B2 | 9/2013 | Bouadi |
| 8,529,630 | B2 | 9/2013 | Bojarski et al. |
| 8,532,806 | B1 | 9/2013 | Masson |
| 8,532,807 | B2 | 9/2013 | Metzger |
| 8,535,319 | B2 | 9/2013 | Ball |
| 8,545,509 | B2 | 10/2013 | Park et al. |
| 8,545,569 | B2 | 10/2013 | Fitz et al. |
| 8,551,099 | B2 | 10/2013 | Lang et al. |
| 8,551,102 | B2 | 10/2013 | Fitz et al. |
| 8,551,103 | B2 | 10/2013 | Fitz et al. |
| 8,551,169 | B2 | 10/2013 | Fitz et al. |
| 8,556,906 | B2 | 10/2013 | Fitz et al. |
| 8,556,907 | B2 | 10/2013 | Fitz et al. |
| 8,556,971 | B2 | 10/2013 | Lang |
| 8,556,983 | B2 | 10/2013 | Bojarski et al. |
| 8,561,278 | B2 | 10/2013 | Fitz et al. |
| 8,562,611 | B2 | 10/2013 | Fitz et al. |
| 8,562,618 | B2 | 10/2013 | Fitz et al. |
| 8,568,479 | B2 | 10/2013 | Fitz et al. |
| 8,568,480 | B2 | 10/2013 | Fitz et al. |
| 8,585,708 | B2 | 11/2013 | Fitz et al. |
| 8,617,172 | B2 | 12/2013 | Fitz et al. |
| 8,617,242 | B2 | 12/2013 | Philipp |
| 8,623,026 | B2 | 1/2014 | Wong et al. |
| 8,634,617 | B2 | 1/2014 | Tsougarakis et al. |
| 8,634,618 | B2 | 1/2014 | Zug et al. |
| 8,638,998 | B2 | 1/2014 | Steines et al. |
| 8,641,716 | B2 | 2/2014 | Fitz et al. |
| 8,657,827 | B2 | 2/2014 | Fitz et al. |
| 8,682,052 | B2 | 3/2014 | Fitz et al. |
| 8,690,945 | B2 | 4/2014 | Fitz et al. |
| 8,709,089 | B2 | 4/2014 | Lang et al. |
| 8,731,885 | B2 | 5/2014 | Lannotti et al. |
| 8,734,455 | B2 | 5/2014 | Park et al. |
| 8,735,773 | B2 | 5/2014 | Lang |
| 8,744,148 | B2 | 6/2014 | Nord et al. |
| 8,764,836 | B2 | 7/2014 | De Wilde et al. |
| 8,768,028 | B2 | 7/2014 | Lang et al. |
| 8,771,365 | B2 | 7/2014 | Bojarski et al. |
| 8,774,900 | B2 | 7/2014 | Buly et al. |
| 8,775,133 | B2 | 7/2014 | Schroeder |
| 8,777,875 | B2 | 7/2014 | Park |
| 8,801,719 | B2 | 8/2014 | Park et al. |
| 8,808,302 | B2 | 8/2014 | Roose et al. |
| 8,814,942 | B2 | 8/2014 | Anthony et al. |
| 8,830,233 | B2 | 9/2014 | Friedland et al. |
| 8,843,229 | B2 | 9/2014 | Vanasse et al. |
| 8,864,769 | B2 | 10/2014 | Stone et al. |
| 8,864,834 | B2 | 10/2014 | Boileau et al. |
| 8,882,847 | B2 | 11/2014 | Burdulis, Jr. et al. |
| 8,884,618 | B2 | 11/2014 | Mahfouz |
| 8,888,855 | B2 | 11/2014 | Roche et al. |

(56) References Cited

U.S. PATENT DOCUMENTS 8,898,043 B2 11/2014 Ashby et al.
8,903,530 B2 12/2014 Metzger
8,906,107 B2 12/2014 Bojarski et al.
8,926,706 B2 1/2015 Bojarski et al.
8,932,361 B2 1/2015 Tornier et al.
8,932,363 B2 1/2015 Tsougarakis et al.
8,934,961 B2 1/2015 Lakin et al.
8,945,230 B2 2/2015 Lang et al.
8,951,259 B2 2/2015 Fitz et al.
8,951,260 B2 2/2015 Lang et al.
8,965,088 B2 2/2015 Tsougarakis et al.
8,971,606 B2 3/2015 Chaoui
8,974,539 B2 3/2015 Bojarski et al.
8,984,731 B2 3/2015 Broeck et al.
8,986,309 B1 3/2015 Murphy
8,989,460 B2 3/2015 Mahfouz
8,990,052 B2 3/2015 Lavallee et al.
8,992,533 B2 3/2015 Blain et al.
8,992,538 B2 3/2015 Keefer
8,998,915 B2 4/2015 Fitz et al.
9,011,456 B2 4/2015 Ranawat et al.
9,020,788 B2 4/2015 Lang
9,023,050 B2 5/2015 Lang et al.
9,055,953 B2 6/2015 Lang et al.
9,060,788 B2 6/2015 Bollinger
9,066,728 B2 6/2015 Burdulis, Jr. et al.
9,066,806 B2 6/2015 Phipps
9,072,531 B2 7/2015 Fitz et al.
9,084,617 B2 7/2015 Lang et al.
9,095,353 B2 8/2015 Burdulis, Jr. et al.
9,095,375 B2 8/2015 Haimerl et al.
9,107,679 B2 8/2015 Lang et al.
9,107,680 B2 8/2015 Fitz et al.
9,113,921 B2 8/2015 Lang et al.
9,125,672 B2 9/2015 Fitz et al.
9,126,673 B1 9/2015 Green et al.
9,138,258 B2 9/2015 Geebelen
9,180,015 B2 11/2015 Fitz et al.
9,186,161 B2 11/2015 Lang et al.
9,186,254 B2 11/2015 Fitz et al.
9,198,732 B2 12/2015 Iannotti et al.
9,204,977 B2 12/2015 Bollinger
9,211,199 B2 12/2015 Ratron
9,216,025 B2 12/2015 Fitz et al.
9,220,516 B2 12/2015 Lang et al.
9,220,517 B2 12/2015 Lang et al.
9,232,955 B2 1/2016 Bonin, Jr. et al.
9,237,950 B2 1/2016 Hensley et al.
9,241,724 B2 1/2016 Lang et al.
9,241,725 B2 1/2016 Lang et al.
9,278,413 B2 3/2016 Sperling
9,289,221 B2 3/2016 Gelaude et al.
9,295,481 B2 3/2016 Fitz et al.
9,295,482 B2 3/2016 Fitz et al.
9,301,768 B2 4/2016 Buza et al.
9,301,812 B2 4/2016 Kehres et al.
9,308,005 B2 4/2016 Fitz et al.
9,308,053 B2 4/2016 Bojarski et al.
9,308,091 B2 4/2016 Lang
9,314,256 B2 4/2016 Fitz et al.
9,320,608 B2 4/2016 Sperling
9,320,620 B2 4/2016 Bojarski et al.
9,326,780 B2 5/2016 Wong et al.
9,333,085 B2 5/2016 Fitz et al.
9,345,548 B2 5/2016 Schoenefeld et al.
9,351,743 B2 5/2016 Kehres et al.
9,358,018 B2 6/2016 Fitz et al.
9,381,025 B2 7/2016 Fitz et al.
9,381,026 B2 7/2016 Trouilloud et al.
9,386,994 B2 7/2016 Agnihotri et al.
9,387,083 B2 7/2016 Al Hares et al.
9,402,726 B2 8/2016 Linderman et al.
9,408,615 B2 8/2016 Fitz et al.
9,408,616 B2 8/2016 Kehres et al.
9,408,686 B1 8/2016 Miller et al.
9,408,698 B2 8/2016 Miles et al.
9,414,928 B2 8/2016 Sperling
9,421,021 B2 8/2016 Keppler
9,439,767 B2 9/2016 Bojarski et al.
9,451,973 B2 9/2016 Heilman et al.
9,486,226 B2 11/2016 Chao
9,495,483 B2 11/2016 Steines et al.
9,498,233 B2 11/2016 Eash
9,504,579 B2 11/2016 Mahfouz et al.
9,517,134 B2 12/2016 Lang
9,539,013 B2 1/2017 Katrana et al.
9,554,910 B2 1/2017 Vanasse et al.
9,575,931 B2 2/2017 Ratron
9,579,106 B2 2/2017 Lo et al.
9,579,110 B2 2/2017 Bojarski et al.
9,592,128 B2 3/2017 Phipps
9,597,201 B2 3/2017 Bollinger
9,603,711 B2 3/2017 Bojarski et al.
9,615,834 B2 4/2017 Agnihotri et al.
9,615,840 B2 4/2017 Iannotti et al.
9,636,229 B2 5/2017 Lang et al.
9,646,113 B2 5/2017 Park et al.
9,649,170 B2 5/2017 Park et al.
9,662,214 B2 5/2017 Li et al.
9,668,873 B2 6/2017 Winslow et al.
9,675,461 B2 6/2017 Mahfouz
9,675,471 B2 6/2017 Bojarski et al.
9,681,956 B2 6/2017 Al Hares et al.
9,684,768 B2 6/2017 Lavallee et al.
9,687,945 B2 6/2017 Steines et al.
9,693,785 B2 7/2017 Theiss et al.
9,700,420 B2 7/2017 Fitz et al.
9,700,971 B2 7/2017 Lang
9,713,533 B2 7/2017 Taylor et al.
9,713,539 B2 7/2017 Haimerl et al.
9,715,563 B1 7/2017 Schroeder
9,717,508 B2 8/2017 Iannotti et al.
9,737,367 B2 8/2017 Steines et al.
9,741,263 B2 8/2017 Iannotti et al.
9,757,238 B2 9/2017 Metzger
9,763,682 B2 9/2017 Bettenga
9,770,335 B2 9/2017 Sperling
9,775,680 B2 10/2017 Bojarski et al.
9,795,393 B2 10/2017 Hughes et al.
9,808,261 B2 11/2017 Gelaude et al.
9,814,533 B2 11/2017 Park et al.
9,820,868 B2 11/2017 Witt et al.
9,839,438 B2 12/2017 Eash
9,849,019 B2 12/2017 Miller et al.
9,872,773 B2 1/2018 Lang et al.
9,877,790 B2 1/2018 Bojarski et al.
9,895,230 B2 2/2018 Mahfouz
9,913,691 B2 3/2018 Brooks
9,913,723 B2 3/2018 Fitz et al.
9,925,048 B2 3/2018 Winslow et al.
9,936,962 B2 4/2018 Heilman et al.
9,937,046 B2 4/2018 Mahfouz
9,943,370 B2 4/2018 Asseln et al.
9,956,047 B2 5/2018 Bojarski et al.
9,956,048 B2 5/2018 Bojarski et al.
9,987,024 B2 6/2018 Frey et al.
9,993,341 B2 6/2018 Vanasse et al.
10,010,334 B2 7/2018 Keppler
10,010,431 B2 7/2018 Eraly et al.
10,019,551 B2 7/2018 Zellner et al.
10,022,137 B2 7/2018 Theiss et al.
10,034,757 B2 7/2018 Kovacs et al.
10,052,114 B2 8/2018 Keppler et al.
10,052,206 B2 8/2018 Mahfouz
10,085,839 B2 10/2018 Wong et al.
10,092,419 B2 10/2018 Hananouchi et al.
10,102,309 B2 10/2018 Mckinnon et al.
10,130,378 B2 11/2018 Bryan
10,159,513 B2 12/2018 Pavlovskaia et al.
10,172,715 B2 1/2019 de Wilde et al.
10,182,870 B2 1/2019 Park et al.
10,195,036 B2 2/2019 Ratron
10,195,043 B2 2/2019 Taylor et al.
10,206,688 B2 2/2019 Park et al.

(56) References Cited

U.S. PATENT DOCUMENTS 10,213,311 B2 2/2019 Mahfouz
10,251,755 B2 4/2019 Boileau et al.
10,262,084 B2 4/2019 LaVallee et al.
10,349,953 B2 7/2019 Park et al.
10,405,993 B2 9/2019 Deransart et al.
10,413,416 B2 9/2019 Boileau et al.
10,426,493 B2 10/2019 Kehres et al.
10,426,549 B2 10/2019 Kehres et al.
10,441,298 B2 10/2019 Eash
10,537,390 B2 1/2020 Varadarajan et al.
10,543,100 B2 1/2020 Couture et al.
10,575,958 B2 3/2020 Cardon et al.
10,600,515 B2 3/2020 Otto et al.
10,624,655 B2 4/2020 Iannotti et al.
10,624,755 B2 4/2020 Amis et al.
10,660,709 B2 5/2020 Chaoui
10,667,867 B2 6/2020 Gangwar et al.
10,675,063 B2 6/2020 Pavlovskaia et al.
10,722,310 B2 7/2020 Luby
10,736,697 B2 8/2020 Chaoui et al.
10,762,623 B2 9/2020 Geebelen et al.
10,842,510 B2 11/2020 Heilman et al.
10,842,512 B2 11/2020 Bonin, Jr. et al.
10,888,378 B2 1/2021 Walch
10,905,562 B2 2/2021 Sbaiz et al.
10,912,571 B2 2/2021 Pavlovskaia et al.
10,922,448 B2 2/2021 McKinnon et al.
10,925,658 B2 2/2021 Hopkins
10,973,535 B2 4/2021 Iannotti et al.
10,973,580 B2 4/2021 Berend et al.
11,033,335 B2 6/2021 Zhang
11,039,889 B2 6/2021 Frey et al.
11,051,830 B2 7/2021 Jaramaz et al.
11,071,592 B2 7/2021 Mcguan et al.
11,083,525 B2 8/2021 Varadarajan et al.
11,090,161 B2 8/2021 Hodorek
11,129,678 B2 9/2021 Park
11,134,963 B2 10/2021 Buza et al.
11,141,276 B2 10/2021 Kehres
11,166,733 B2 11/2021 Neichel et al.
11,166,764 B2 11/2021 Roh et al.
11,179,249 B2 11/2021 Deransart et al.
11,185,417 B2 11/2021 Boileau et al.
11,202,675 B2 12/2021 Uhde et al.
11,213,305 B2 1/2022 Iannotti et al.
11,234,721 B2 2/2022 Gargac et al.
11,253,323 B2 2/2022 Hughes et al.
11,278,299 B2 3/2022 Neichel et al.
11,278,413 B1 3/2022 Lang
11,298,118 B1 4/2022 Koo
11,298,140 B2 4/2022 Wilkinson et al.
11,298,142 B2 4/2022 Park et al.
11,298,188 B2 4/2022 Kehres et al.
11,298,189 B2 4/2022 Kelman et al.
11,337,762 B2 5/2022 McKinnon et al.
11,344,370 B2 5/2022 Park et al.
11,399,851 B2 8/2022 Neichel et al.
11,399,894 B2 8/2022 Chaoui et al.
11,410,769 B1 8/2022 Yildirim
11,419,618 B2 8/2022 Kehres et al.
11,419,680 B2 8/2022 Kontaxis et al.
11,432,931 B2 9/2022 Lang
11,432,934 B2 9/2022 Couture et al.
11,443,846 B2 9/2022 Schoenefeld et al.
11,471,303 B2 10/2022 Christopher
11,488,721 B2 11/2022 Otto et al.
11,490,965 B2 11/2022 Bischoff et al.
11,490,966 B2 11/2022 Roche et al.
11,559,403 B2 1/2023 Kehres
11,596,479 B2 3/2023 Mcguan et al.
11,602,360 B2 3/2023 Heilman et al.
11,617,591 B2 4/2023 Eash
11,621,086 B2 4/2023 Spångberg et al.
11,622,818 B2 4/2023 Siemionow et al.
11,653,976 B2 5/2023 Bonny et al.
11,660,197 B1 5/2023 Lang
11,696,833 B2 7/2023 Casey et al.
11,712,302 B2 8/2023 Walch
11,717,412 B2 8/2023 Casey et al.
11,730,497 B2 8/2023 Iannotti et al.
11,737,883 B2 8/2023 Metcalfe et al.
11,751,946 B2 9/2023 Gangwar et al.
11,752,000 B2 9/2023 Terrill
11,766,268 B2 9/2023 Iannotti et al.
11,766,336 B2 9/2023 Penninger et al.
11,819,415 B2 11/2023 Metcalfe et al.
11,847,755 B2 12/2023 Park et al.
11,850,158 B2 12/2023 Simoes et al.
11,883,040 B2 1/2024 Bonin, Jr et al.
2001/0047210 A1 11/2001 Wolf
2002/0007294 A1 1/2002 Bradbury et al.
2002/0082741 A1 6/2002 Mazumder et al.
2003/0028253 A1 2/2003 Stone et al.
2003/0074080 A1 4/2003 Murray
2003/0139818 A1 7/2003 Rogers et al.
2004/0039259 A1 2/2004 Krause et al.
2004/0064189 A1 4/2004 Maroney et al.
2004/0102866 A1 5/2004 Harris et al.
2004/0133276 A1 7/2004 Lang et al.
2004/0138754 A1 7/2004 Lang et al.
2004/0171924 A1 9/2004 Mire et al.
2004/0181144 A1 9/2004 Cinquin et al.
2004/0236424 A1 11/2004 Berez et al.
2004/0243481 A1 12/2004 Bradbury et al.
2005/0049709 A1 3/2005 Tornier
2005/0065617 A1 3/2005 Barrera et al.
2005/0065628 A1 3/2005 Roose
2005/0087047 A1 4/2005 Farrar
2005/0098915 A1 5/2005 Long et al.
2005/0112397 A1 5/2005 Rolfe et al.
2005/0197814 A1 9/2005 Aram
2005/0216305 A1 9/2005 Funderud
2006/0079963 A1 4/2006 Hansen
2006/0095047 A1 5/2006 de la Barrera
2006/0136058 A1 6/2006 Pietrzak
2007/0005067 A1* 1/2007 Dross .................... A61B 17/17 606/232
2007/0089518 A1 4/2007 Ericson et al.
2007/0118055 A1 5/2007 McCombs
2007/0118243 A1 5/2007 Schroeder et al.
2007/0191741 A1 8/2007 Tsai et al.
2007/0198094 A1 8/2007 Berelsman et al.
2007/0203605 A1 8/2007 Melton et al.
2007/0233141 A1 10/2007 Park et al.
2007/0244563 A1 10/2007 Roche et al.
2007/0249967 A1 10/2007 Buly et al.
2008/0014082 A1 1/2008 Kunz et al.
2008/0109000 A1 5/2008 Maroney et al.
2008/0183297 A1 7/2008 Boileau et al.
2008/0188945 A1 8/2008 Boyce et al.
2008/0228269 A1 9/2008 McLeod et al.
2008/0243127 A1 10/2008 Lang et al.
2008/0269596 A1 10/2008 Revie et al.
2008/0269906 A1 10/2008 Lannotti et al.
2008/0281328 A1 11/2008 Lang et al.
2008/0281329 A1 11/2008 Fitz et al.
2008/0281426 A1 11/2008 Fitz et al.
2008/0287954 A1 11/2008 Kunz et al.
2009/0089034 A1 4/2009 Penney et al.
2009/0216285 A1 8/2009 Ek et al.
2009/0226068 A1 9/2009 Fitz et al.
2009/0264894 A1 10/2009 Wasielewski
2009/0276045 A1 11/2009 Lang
2009/0292464 A1 11/2009 Fuchs et al.
2009/0318929 A1 12/2009 Tornier et al.
2010/0023015 A1 1/2010 Park
2010/0082035 A1* 4/2010 Keefer ............... A61B 17/1666 606/91
2010/0087927 A1 4/2010 Roche et al.
2010/0114326 A1 5/2010 Winslow et al.
2010/0160917 A1 6/2010 Fitz et al.
2010/0191100 A1 7/2010 Anderson et al.
2010/0217270 A1 8/2010 Polinski et al.
2010/0222781 A1 9/2010 Collazo et al.

(56) References Cited

U.S. PATENT DOCUMENTS

2010/0292963 A1 11/2010 Schroeder
2010/0303313 A1 12/2010 Lang et al.
2010/0305573 A1 12/2010 Fitz et al.
2010/0305574 A1 12/2010 Fitz et al.
2011/0029088 A1 2/2011 Raucher et al.
2011/0035013 A1 2/2011 Winslow et al.
2011/0040334 A1 2/2011 Kaes et al.
2011/0046735 A1 2/2011 Metzger et al.
2011/0054478 A1 3/2011 Vanasse et al.
2011/0118846 A1 5/2011 Katrana et al.
2011/0119884 A1 5/2011 Ratron
2011/0137427 A1 6/2011 Lappin et al.
2011/0152869 A1 6/2011 Ek et al.
2011/0166661 A1 7/2011 Boileau et al.
2011/0190775 A1 8/2011 Ure
2011/0295329 A1 12/2011 Fitz et al.
2011/0304332 A1 12/2011 Mahfouz
2012/0010711 A1 1/2012 Antonyshyn et al.
2012/0041446 A1 2/2012 Wong et al.
2012/0041564 A1 2/2012 Landon
2012/0078258 A1 3/2012 Lo et al.
2012/0101503 A1 4/2012 Lang et al.
2012/0116203 A1 5/2012 Vancraen et al.
2012/0130434 A1 5/2012 Stemniski
2012/0141034 A1 6/2012 Iannotti et al.
2012/0143267 A1* 6/2012 Iannotti .............. A61B 17/1746 606/86 R
2012/0245647 A1 9/2012 Kunz et al.
2012/0253350 A1 10/2012 Anthony et al.
2012/0276509 A1 11/2012 Iannotti et al.
2012/0279933 A1 11/2012 Hensler et al.
2012/0289965 A1 11/2012 Gelaude et al.
2012/0296339 A1 11/2012 Ianotti et al.
2012/0303035 A1 11/2012 Geebelen
2013/0024580 A1 1/2013 Tsai et al.
2013/0053968 A1 2/2013 Nardini et al.
2013/0110116 A1 5/2013 Kehres et al.
2013/0110471 A1 5/2013 Lang et al.
2013/0114873 A1 5/2013 Chaoui
2013/0172898 A1 7/2013 Iannotti et al.
2013/0190882 A1 7/2013 Humphrey
2013/0211531 A1 8/2013 Steines et al.
2013/0261629 A1 10/2013 Anthony et al.
2013/0274752 A1 10/2013 Trouilloud et al.
2013/0338673 A1 12/2013 Keppler
2014/0039633 A1 2/2014 Roche et al.
2014/0159282 A1 6/2014 Smith et al.
2014/0163564 A1* 6/2014 Bollinger ........... A61B 17/1746 606/91
2014/0236158 A1* 8/2014 Gelaude ............. A61B 17/1778 29/592
2014/0257304 A1 9/2014 Eash
2014/0257495 A1 9/2014 Goldberg
2014/0257499 A1 9/2014 Winslow et al.
2014/0276867 A1 9/2014 Kelley et al.
2014/0303738 A1 10/2014 Deffenbaugh et al.
2014/0303938 A1 10/2014 Schoenefeld et al.
2014/0303990 A1 10/2014 Schoenefeld et al.
2014/0371863 A1 12/2014 Vanasse et al.
2015/0045903 A1 2/2015 Neal
2015/0052586 A1 2/2015 Mills
2015/0073424 A1 3/2015 Couture et al.
2015/0093283 A1 4/2015 Miller et al.
2015/0105787 A1 4/2015 Tornier et al.
2015/0112348 A1 4/2015 Schoenefeld et al.
2015/0150688 A1 6/2015 Vanasse et al.
2015/0223941 A1 8/2015 Lang
2015/0250552 A1 9/2015 Radermacher et al.
2015/0250597 A1 9/2015 Lang et al.
2015/0250601 A1 9/2015 Humphrey
2015/0320430 A1 11/2015 Kehres et al.
2015/0328004 A1 11/2015 Mafhouz
2015/0342739 A1 12/2015 Mahfouz
2016/0015466 A1 1/2016 Park et al.
2016/0030196 A1 2/2016 Eraly et al.
2016/0051367 A1 2/2016 Gervasi et al.
2016/0067049 A1 3/2016 Flaherty et al.
2016/0074052 A1 3/2016 Keppler et al.
2016/0100907 A1 4/2016 Gomes
2016/0120555 A1 5/2016 Bonin, Jr. et al.
2016/0136904 A1 5/2016 Murai et al.
2016/0143744 A1 5/2016 Bojarski et al.
2016/0143749 A1 5/2016 Holovacs et al.
2016/0157937 A1 6/2016 Kehres et al.
2016/0166392 A1 6/2016 Vanasse et al.
2016/0184104 A1 6/2016 Sperling
2016/0192951 A1 7/2016 Gelaude et al.
2016/0193051 A1 7/2016 Budhabhatti et al.
2016/0213385 A1 7/2016 Iannotti et al.
2016/0242933 A1 8/2016 Deransart et al.
2016/0256222 A1 9/2016 Walch
2016/0270854 A1 9/2016 Chaoui et al.
2016/0296285 A1 10/2016 Chaoui et al.
2016/0296290 A1 10/2016 Furrer et al.
2016/0324648 A1 11/2016 Hodorek et al.
2016/0331467 A1 11/2016 Slamin et al.
2016/0345987 A1 12/2016 Guilloux et al.
2016/0374697 A1 12/2016 Kehres et al.
2017/0000614 A1 1/2017 Mahfouz
2017/0000615 A1 1/2017 Mahfouz
2017/0027587 A1 2/2017 Fraone et al.
2017/0027593 A1 2/2017 Bojarski et al.
2017/0035513 A1 2/2017 Mahfouz et al.
2017/0056024 A1 3/2017 Chao
2017/0071748 A1 3/2017 Humphrey
2017/0079803 A1 3/2017 Lang
2017/0105841 A1 4/2017 Vanasse et al.
2017/0105843 A1 4/2017 Britton et al.
2017/0112626 A1 4/2017 Miller et al.
2017/0119531 A1 5/2017 Bojarski et al.
2017/0143499 A1 5/2017 Phipps
2017/0151058 A1 6/2017 Sperling
2017/0216038 A1 8/2017 Lang et al.
2017/0231783 A1 8/2017 Lang et al.
2017/0249440 A1 8/2017 Lang et al.
2017/0258598 A1 9/2017 Radermacher et al.
2017/0273795 A1 9/2017 Neichel et al.
2017/0273800 A1 9/2017 Emerick et al.
2017/0273801 A1 9/2017 Hodorek
2017/0281357 A1 10/2017 Taylor et al.
2017/0296347 A1 10/2017 Chua et al.
2017/0304063 A1 10/2017 Hatzidakis et al.
2017/0340449 A1 11/2017 Deransart et al.
2017/0360567 A1 12/2017 Fitz et al.
2017/0367766 A1 12/2017 Mahfouz
2017/0367828 A1 12/2017 Steines et al.
2017/0367834 A1 12/2017 Fitz et al.
2018/0014835 A1 1/2018 Lo et al.
2018/0028325 A1 2/2018 Bojarski et al.
2018/0036019 A1 2/2018 Iannotti et al.
2018/0161176 A1 6/2018 Vivanz et al.
2018/0228614 A1 8/2018 Lang et al.
2018/0233222 A1 8/2018 Daley et al.
2018/0235642 A1 8/2018 Amis et al.
2018/0235706 A1 8/2018 Asseln et al.
2018/0235762 A1 8/2018 Radermacher et al.
2018/0263782 A1 9/2018 Lang et al.
2018/0289380 A1 10/2018 Mauldin et al.
2018/0325526 A1 11/2018 Haddad
2019/0000629 A1 1/2019 Winslow
2019/0015113 A1 1/2019 Morvan
2019/0015116 A1 1/2019 Neichel et al.
2019/0015117 A1 1/2019 Neichel et al.
2019/0015118 A1 1/2019 Neichel et al.
2019/0015119 A1 1/2019 Athwal et al.
2019/0015221 A1 1/2019 Neichel et al.
2019/0021866 A1 1/2019 Vanasse et al.
2019/0029757 A1 1/2019 Roh et al.
2019/0038360 A1 2/2019 Chaoui
2019/0069913 A1 3/2019 Iannotti et al.
2019/0090952 A1 3/2019 Bonny et al.
2019/0142519 A1 5/2019 Siemionow et al.
2019/0201005 A1 7/2019 Schoenefeld et al.
2019/0269415 A1 9/2019 Lo et al.

(56) References Cited

U.S. PATENT DOCUMENTS

| | | | |
|---|---|---|---|
| 2019/0365473 | A1 | 12/2019 | Kehres et al. |
| 2020/0030034 | A1 | 1/2020 | Kontaxis et al. |
| 2020/0078180 | A1 | 3/2020 | Casey |
| 2020/0113632 | A1 | 4/2020 | Varadarajan et al. |
| 2020/0155323 | A1 | 5/2020 | Lang et al. |
| 2020/0170802 | A1 | 6/2020 | Casey |
| 2020/0188121 | A1 | 6/2020 | Boux De Casson et al. |
| 2020/0188134 | A1 | 6/2020 | Mullen et al. |
| 2020/0281728 | A1 | 9/2020 | Kulper et al. |
| 2020/0330161 | A1 | 10/2020 | Chaoui et al. |
| 2020/0405330 | A1 | 12/2020 | Bonin, Jr. et al. |
| 2021/0030477 | A1 | 2/2021 | Zuhars et al. |
| 2021/0045888 | A1 | 2/2021 | Sbaiz et al. |
| 2021/0068844 | A1 | 3/2021 | Lo et al. |
| 2021/0085475 | A1 | 3/2021 | Hodorek et al. |
| 2021/0128179 | A1 | 5/2021 | Dupuis et al. |
| 2021/0128244 | A1 | 5/2021 | Couture et al. |
| 2021/0196290 | A1 | 7/2021 | Iannotti et al. |
| 2021/0228277 | A1 | 7/2021 | Chaoui et al. |
| 2021/0259844 | A1 | 8/2021 | Penninger et al. |
| 2021/0307833 | A1 | 10/2021 | Farley et al. |
| 2021/0307911 | A1 | 10/2021 | Metcalfe et al. |
| 2021/0315642 | A1 | 10/2021 | Mcguan et al. |
| 2021/0322130 | A1 | 10/2021 | Penney et al. |
| 2021/0330389 | A1 | 10/2021 | Varadarajan et al. |
| 2021/0338435 | A1 | 11/2021 | Hodorek |
| 2021/0386435 | A1 | 12/2021 | Buza et al. |
| 2022/0022895 | A1 | 1/2022 | Neichel et al. |
| 2022/0031475 | A1 | 2/2022 | Deransart et al. |
| 2022/0047278 | A1 | 2/2022 | Fitz et al. |
| 2022/0054197 | A1 | 2/2022 | Plessers et al. |
| 2022/0096240 | A1 | 3/2022 | Neichel et al. |
| 2022/0110644 | A1 | 4/2022 | Gargac et al. |
| 2022/0110685 | A1 | 4/2022 | Mcguan et al. |
| 2022/0125515 | A1 | 4/2022 | Mcguan et al. |
| 2022/0148454 | A1 | 5/2022 | Jaramaz et al. |
| 2022/0160376 | A1 | 5/2022 | Neichel et al. |
| 2022/0160405 | A1 | 5/2022 | Casey et al. |
| 2022/0160439 | A1 | 5/2022 | Ryan et al. |
| 2022/0183757 | A1 | 6/2022 | Caldera et al. |
| 2022/0202497 | A1 | 6/2022 | Janna et al. |
| 2022/0211507 | A1 | 7/2022 | Simoes et al. |
| 2022/0249168 | A1 | 8/2022 | Besier et al. |
| 2022/0257321 | A1 | 8/2022 | Kehres et al. |
| 2022/0273450 | A1 | 9/2022 | Steines et al. |
| 2022/0296259 | A1 | 9/2022 | Shah |
| 2022/0313440 | A1 | 10/2022 | Metcalfe et al. |
| 2022/0330957 | A1 | 10/2022 | Neichel et al. |
| 2022/0338933 | A1 | 10/2022 | Metcalfe et al. |
| 2022/0338998 | A1 | 10/2022 | Sperling |
| 2022/0346968 | A1 | 11/2022 | Pettersson et al. |
| 2022/0351828 | A1 | 11/2022 | Chaoui |
| 2022/0370142 | A1 | 11/2022 | Schoenefeld et al. |
| 2022/0387110 | A1 | 12/2022 | Chaoui |
| 2022/0395376 | A1 | 12/2022 | Poon et al. |
| 2023/0000645 | A1 | 1/2023 | Christopher |
| 2023/0045575 | A1 | 2/2023 | Lang et al. |
| 2023/0048940 | A1 | 2/2023 | Kontaxis et al. |
| 2023/0061695 | A1 | 3/2023 | Couture et al. |
| 2023/0079807 | A1 | 3/2023 | Metcalfe et al. |
| 2023/0085093 | A1 | 3/2023 | Chaoui et al. |
| 2023/0109478 | A1 | 4/2023 | Chaoui et al. |
| 2023/0139531 | A1 | 5/2023 | Roche et al. |
| 2023/0148085 | A1 | 5/2023 | Paul et al. |
| 2023/0181257 | A1 | 6/2023 | Mcguan et al. |
| 2023/0248435 | A1 | 8/2023 | Bonny et al. |
| 2023/0317298 | A1 | 10/2023 | Spångberg et al. |
| 2023/0329791 | A1 | 10/2023 | Chaoui et al. |
| 2023/0346397 | A1 | 11/2023 | Iannotti et al. |
| 2023/0346480 | A1 | 11/2023 | Walch |
| 2023/0355401 | A1 | 11/2023 | Metcalfe et al. |
| 2023/0363915 | A1 | 11/2023 | Metcalfe et al. |
| 2023/0372018 | A1 | 11/2023 | Gangwar et al. |
| 2023/0372111 | A1 | 11/2023 | Terrill |

FOREIGN PATENT DOCUMENTS

| | | | |
|---|---|---|---|
| CA | 2927811 | | 4/2015 |
| CA | 2938709 | | 5/2015 |
| CA | 3203261 | A1 | 7/2022 |
| EP | 1 249 213 | | 10/2002 |
| EP | 1 265 555 | | 12/2002 |
| EP | 1 563 810 | | 8/2005 |
| EP | 1 862 151 | | 12/2007 |
| EP | 1 902 689 | | 3/2008 |
| EP | 1 952 788 | | 8/2008 |
| EP | 2 135 576 | | 12/2009 |
| EP | 1 917 051 | B1 | 6/2010 |
| EP | 2 243 445 | | 10/2010 |
| EP | 2 324 801 | A1 | 5/2011 |
| EP | 2 501 313 | | 9/2012 |
| EP | 2 544 601 | | 1/2013 |
| EP | 2583242 | | 4/2013 |
| EP | 1858430 | B1 | 10/2013 |
| EP | 2471483 | B1 | 10/2013 |
| EP | 2670314 | B1 | 8/2014 |
| EP | 2 845 547 | | 3/2015 |
| EP | 2856951 | A1 | 4/2015 |
| EP | 2 965 720 | | 1/2016 |
| EP | 1323395 | B1 | 8/2016 |
| EP | 3057518 | | 8/2016 |
| EP | 3057524 | | 8/2016 |
| EP | 3065671 | | 9/2016 |
| EP | 3068317 | | 9/2016 |
| EP | 2 874 570 | B1 | 1/2017 |
| EP | 3 117 801 | | 1/2017 |
| EP | 2244654 | B1 | 3/2017 |
| EP | 2770920 | B1 | 7/2017 |
| EP | 2770919 | B1 | 8/2017 |
| EP | 2303192 | B1 | 11/2018 |
| EP | 3760142 | A1 | 1/2021 |
| EP | 3248553 | B1 | 3/2021 |
| EP | 3845154 | A1 | 7/2021 |
| EP | 3481318 | B1 | 9/2022 |
| FR | 2 579 454 | | 10/1986 |
| FR | 2 859 099 | | 3/2005 |
| FR | 2962573 | A1 | 1/2012 |
| FR | 2982694 | B1 | 11/2016 |
| FR | 2982979 | B1 | 11/2016 |
| FR | 2982693 | B1 | 12/2016 |
| GB | 2501494 | A | 10/2013 |
| WO | WO 93/025157 | | 12/1993 |
| WO | WO 00/35346 | | 6/2000 |
| WO | WO 00/59411 | | 10/2000 |
| WO | WO 02/061688 | | 8/2002 |
| WO | 2005016123 | A2 | 2/2005 |
| WO | 2006106419 | A2 | 10/2006 |
| WO | 2008021494 | A2 | 2/2008 |
| WO | WO 2010/120346 | | 10/2010 |
| WO | 2010129870 | A1 | 11/2010 |
| WO | WO 2011/110374 | | 9/2011 |
| WO | 2011142998 | A1 | 11/2011 |
| WO | WO 2011/154891 | | 12/2011 |
| WO | WO 2011/157961 | | 12/2011 |
| WO | WO 2012/021241 | | 2/2012 |
| WO | WO 2012/058349 | | 5/2012 |
| WO | WO 2012/125319 | | 9/2012 |
| WO | 2012141790 | A1 | 10/2012 |
| WO | 2012170376 | A2 | 12/2012 |
| WO | WO 2013/060851 | | 5/2013 |
| WO | WO 2013/062848 | | 5/2013 |
| WO | WO 2013/062851 | | 5/2013 |
| WO | WO 2013/142998 | | 10/2013 |
| WO | WO 2014/020561 | | 2/2014 |
| WO | WO 2014/035991 | | 3/2014 |
| WO | 2014145267 | A1 | 9/2014 |
| WO | WO 2014/180972 | | 11/2014 |
| WO | 2015018921 | A1 | 2/2015 |
| WO | WO 2015/052586 | | 4/2015 |
| WO | WO 2015/056097 | | 4/2015 |
| WO | 2015071757 | A1 | 5/2015 |
| WO | WO 2015/068035 | | 5/2015 |
| WO | WO 2015/071757 | | 5/2015 |
| WO | WO 2015/175397 | | 11/2015 |

(56) References Cited

FOREIGN PATENT DOCUMENTS

| | | |
|---|---|---|
| WO | WO 2015/185219 | 12/2015 |
| WO | WO 2017/091657 | 6/2017 |
| WO | WO 2017/105815 | 6/2017 |
| WO | WO 2017/106294 | 6/2017 |
| WO | WO 2017/184792 | 10/2017 |
| WO | WO 2017/214537 | 12/2017 |
| WO | WO 2018/022227 | 2/2018 |
| WO | WO 2019/014278 | 1/2019 |
| WO | WO 2019/014281 | 1/2019 |
| WO | WO 2019/033037 | 2/2019 |

OTHER PUBLICATIONS

Boileau, et al., "The three-dimensional geometry of the proximal humerus: implications for surgical technique and prosthetic design." The Journal of bone and joint surgery. British vol. 79.5 (1997): 857-865.

Habets, et al., Computer assistance in orthopaedic surgery. Technische Universiteit Eindhoven, 2002.

Hempfing, et al. "Surgical landmarks to determine humeral head retrotorsion for hemiarthroplasty in fractures." Journal of shoulder and elbow surgery 10.5 (2001): 460-463.

Ma, et al., "Robust registration for computer-integrated orthopedic surgery: laboratory validation and clinical experience." Medical image analysis 7.3 (2003): 237-250.

"Olympia Total Shoulder System Surgical Technique", Wright Medical Technology, 2001, in 19 pages.

Radermacher, K., et al., "Computer Assisted Orthopaedic Surgery with Image Based Individual Templates," Clinical Orthopaedics and Related Research, No. 354, Sep. 1998, pp. 28-38.

Radermacher, K., et al., "Image Guided Orthopedic Surgery Using Individual Templates: Experimental Results and Aspects of the Development of a Demonstrator for Pelvis Surgery", Health Care Sector, Telematics Applications Program, 1997, pp. 606-615.

Tornier, "Salto Talaris, Total Ankle Prosthesis", 2009.

Valstar, et al. "Towards computer-assisted surgery in shoulder joint replacement." ISPRS journal of photogrammetry and remote sensing 56.5-6 (2002): 326-337.

Valstar, et al. "The use of Roentgen stereophotogrammetry to study micromotion of orthopaedic implants." ISPRS journal of photogrammetry and remote sensing 56.5-6 (2002): 376-389.

Welsh, et al., "CT-based preoperative analysis of scapula morphology and glenohumeral joint geometry." Computer Aided Surgery 8.5 (2003): 264-268.

Zimmer, "Zimmer ® PSI Shoulder Trabecular MetalTM Reverse Glenoid Base Plate Surgical Technique", Dec. 30, 2013.

Extended European Search Report issued in EP Application No. 18187134.4, dated Nov. 22, 2018 in 6 pages.

International Search Report and Written Opinion for PCT/IB2014/002711 dated Mar. 23, 2015 in 12 pages.

Dougherty, "Digital Image Processing for Medical Applications," May 11, 2009 (May 11, 2009), Cambridge University Press, XP002615721.

Gregory, et al.," Accuracy of Glenoid Component Placement in Total Shoulder Arthroplasty and Its Effect on Clinical and Radiological Outcome in a Retrospective, Longitudinal, Monocentric Open Study," PLOS One, p. e75791, Aug. 1, 2013, vol. 8, No. 10.

Iannotti et al., "Prosthetic positioning in total shoulder arthroplasty," Journal of Shoulder and Elbow Surgery, Jan. 1, 2005, vol. 14, No. 1S, pp. S111-S121.

Kobashi et al., "Knowledge-Based Organ Identification from CT Images," Pattern Recognition, Elsevier, GB, vol. 28, No. 4, Apr. 1, 1995 (Apr. 1, 1995), pp. 475-491, XP004013165.

Lee, C.C. et al., "Identifying multiple abdominal organs from CT image series using a multimodule contextual neural network and spatial fuzzy rules", IEEE Transactions on Information Technology in Biomedicine, IEEE Services Center, Los Alamitos, CA, US, vol. 7, No. 3, Sep. 1, 2003 (Sep. 1, 2003) pp. 208-217, XP011100536.

Wu, et al. "An interface for the data exchange between CAS and CAD/CAM systems." International Congress Series. vol. 1256. Elsevier, 2003.

Communication Pursuant to Article 94(3) issued in connection with European Patent Application No. 19759204.1, May 9, 2023, 6 pages.

Communication Pursuant to Article 94(3) issued in connection with European Patent Application No. 18746503.4, Oct. 17, 2023, 5 pages.

Notice of Allowance issued in connection with U.S. Appl. No. 16/648,128, filed Feb. 16, 2024, 9 pages.

First Examination Report from counterpart Australian Application No. 2021201702 dated Dec. 1, 2021, 2 pp.

Marker et al., "Contour-Based Surface Reconstruction using Implicit Curve Fitting, and Distance Field Filtering and Interpolation," vol. Graphics, Jan. 2006, 9 pp.

Nguyen et al., "Design and Development of a Computer Assisted Glenoid Implantation Technique for Shoulder Replacement Surgery," Computer Aided Surgery, vol. 12, No. 3, May 2007, pp. 152-159.

First Examination Report issued in connection with corresponding Australian Patent Application No. 2019236696, Jun. 18, 2020, 4 pages.

International Search Report and Written Opinion of the International Searching Authority issued for PCT Application No. PCT/IB2014/002759 mailed Mar. 27, 2015, 13 pp.

Notice of Acceptance from counterpart Australian Application No. 2021201702 dated Apr. 1, 2022, 3 pp.

Notice of Allowance from counterpart Canadian Application No. 2,927,811 dated Jan. 18, 2022, 1 pp.

Office Action from counterpart Canadian Application No. 2,927,811, dated Apr. 29, 2021, 3 pp.

Office Action from counterpart Canadian Application No. 2,927,811, dated Nov. 17, 2020, 3 pp.

Office Action issued in connection with corresponding Canadian Patent Application No. 2,927,811, May 25, 2020, 3 pages.

Prosecution History from U.S. Appl. No. 15/029,879, dated May 17, 2018 through Dec. 16, 2020, 122 pp.

Prosecution History from U.S. Appl. No. 17/117,546, dated Dec. 10, 2020 through Mar. 14, 2023, 29 pp.

Raaijmakers et al., "A Custom-Made Guide-Wire Positioning Device for Hip Surface Replacement Arthroplasty: Description and First Results," BMC Musculoskeletal Disorders, vol. 11, Jul. 2010, 7 pp.

Response to Office Action dated Dec. 1, 2021, from counterpart Australian Application No. 2021201702 filed Mar. 30, 2022, 1 pp.

Response to Official Action from counterpart Canadian Application No. 2,927,811, dated Apr. 29, 2021, filed Aug. 26, 2021, 8 pp.

Response to Official Action from counterpart Canadian Application No. 2,927,811, dated May 25, 2020, filed Sep. 25, 2020, 19 pp.

Response to Official Action from counterpart Canadian Application No. 2,927,811, dated Nov. 17, 2020, filed Mar. 16, 2021, 15 pp.

Response to Official Action from counterpart Canadian Application No. 2,927,811, dated Oct. 10, 2019, filed Apr. 14, 2020, 11 pp.

Advisory Action from U.S. Appl. No. 16/918,347 dated Aug. 8, 2023, 2 pp.

Boissonnat, J.D., "Shape Reconstruction from Planar Cross Sections," Computer Vision, Graphics, and Image Processing, vol. 44, No. 1, Oct. 1988, 29 pp.

Communication pursuant to Article 94(3) EPC from counterpart European Application No. 19209711.1 dated Dec. 21, 2022, 4 pp.

Examination Report No. 1 from counterpart Australian Application No. 2021203700 dated Dec. 1, 2022, 5 pp.

Extended European Search Report issued in connection with corresponding European Patent Application No. 19209711.1; 12 pages, Mar. 23, 2020.

Final Office Action from U.S. Appl. No. 16/918,347 dated May 30, 2023, 18 pp.

First Examination Report from counterpart Australian Patent Application No. 2021209349 dated Oct. 6, 2022, 4 pp.

First Examination Report issued in connection with Australian Patent Application No. 2019236759 Jul. 17, 2020, 5 pages.

International Preliminary Report on Patentability from International Application No. PCT/IB2014/002819, dated Apr. 12, 2016, 12 pp.

(56) References Cited

OTHER PUBLICATIONS

International Search Report and Written Opinion of the International Searching Authority issued for PCT Application PCT/IB2014/002819 mailed on May 8, 2015.
Notice of Acceptance from counterpart Australian Application No. 2019236759, dated Apr. 27, 2021, 114 pp.
Notice of Acceptance from counterpart Australian Application No. 2021203700, dated Aug. 14, 2023, 41 pp.
Notice of Allowance from counterpart Canadian Application No. 2,927,086, dated Jul. 22, 2021, 1 pp.
Notice of Allowance from U.S. Appl. No. 16/918,347 dated Oct. 2, 2023, 2 pp.
Notice of Allowance from U.S. Appl. No. 16/918,347 dated Sep. 21, 2023, 8 pp.
Notice of Allowance from U.S. Appl. No. 17/874,452 dated Dec. 4, 2023, 5 pp.
Notice of Allowance from U.S. Appl. No. 17/874,452 dated Nov. 15, 2023, 8 pp.
Notice of Allowance from U.S. Appl. No. 17/874,472 dated Feb. 16, 2024, 18 pp.
Notice of Intent to Grant from counterpart Australian Application No. 2021209349 dated May 12, 2023, 3 pp.
Office Action from U.S. Appl. No. 16/918,347 dated Oct. 21, 2022, 19 pp.
Office Action issued in connection with Canadian Patent Application No. 2,927,086, Jan. 20, 2021, 3 pages.
Office Action issued in connection with corresponding Canadian Patent Application No. 2,927,086, Oct. 16, 2019, 7 pages.
Office Action issued in connection with European Patent Application No. 19209711.1, Dec. 22, 2020, 5 pages.
Prosecution History from Australian Patent Application No. 2014333516, dated May 6, 2016 through Oct. 31, 2019, 290 pp.
Prosecution History from European Patent Application No. 14830864.6, dated Jan. 27, 2015 through Dec. 12, 2019, 307 pp.
Prosecution History from U.S. Appl. No. 15/028,497, dated Apr. 4, 2018 through Apr. 6, 2020, 103 pp.
Prosecution History from U.S. Appl. No. 17/229,111, dated Jul. 16, 2021 through Apr. 1, 2022, 53 pp.
Response to Communication from counterpart European Application No. 19209711.1, dated Dec. 22, 2020, filed Mar. 24, 2021, 14 pp.
Response to Communication pursuant to Article 94(3) EPC dated Dec. 21, 2022, from counterpart European Application No. 19209711.1 filed Apr. 20, 2023, 25 pp.
Response to European Search Report from counterpart European Application No. 19209711.1, dated Mar. 23, 2020, filed Oct. 22, 2020, 8 pp.
Response to Examination Report No. 1 from counterpart Australian Application No. 2019236759, dated Jul. 17, 2020, filed Dec. 10, 2020, 77 pp.
Response to Final Office Action dated May 30, 2023 from U.S. Appl. No. 16/918,347, filed Jul. 28, 2023, 12 pp.
Response to Office Action dated Dec. 1, 2022, from counterpart Australian Application No. 2021203700 filed Jul. 4, 2023, 80 pp.
Response to Office Action dated Oct. 21, 2022 from U.S. Appl. No. 16/918,347, filed Feb. 21, 2023, 10 pp.
Response to Office Action dated Oct. 6, 2022, from counterpart Australian Application No. 2021209349 filed May 5, 2023, 74 pp.
Response to Office Action from counterpart Canadian Application No. 2,927,086, dated Jun. 2, 2020, filed Oct. 2, 2020, 14 pp.
Response to Office Action from counterpart Canadian Application No. 2,927,086, dated Oct. 16, 2019, filed Apr. 16, 2020, 10 pp.
Second Examination Report issued in connection with Australian Patent Application No. 2019236759, Dec. 15, 2020, 4 pages.
U.S. Appl. No. 17/874,452, filed Jul. 27, 2022, by Chaoui et al.
Non-Final Office Action issued in connection with U.S. Appl. No. 17/359,745, filed Nov. 26, 2023, 7 pages.
Final Office Action issued in connection with U.S. Appl. No. 16/910,663, filed Nov. 16, 2023, 9 pages.
Linear Actuators Information retrieved from "https://web.archive.org/web/20160309160343/https://www.globalspec.com/learnmore/motion_controls/linear_actuators/linear_actuators" (Year: 2016).
Non-Final Office Action issued in connection with U.S. Appl. No. 17/643,436, filed Jun. 25, 2025, 17 pages.
First Office Action issued in connection with Japanese Patent Application No. 2024-005430, Feb. 12, 2025, 15 pages.
Non-Final Office Action issued in connection with U.S. Appl. No. 17/451,499, filed Feb. 9, 2024, 7 pages.
Non-Final Office Action issued in connection with U.S. Appl. No. 17/643,436, filed May 22, 2024, 13 pages.
First Examination Report issued in connection with Australian Patent Application No. 2024278232, Apr. 28, 2026, 7 pages.

* cited by examiner 100
130
134
132
A
A
A
P
120
110
114
112
X

122
α
P

FIG. 4A
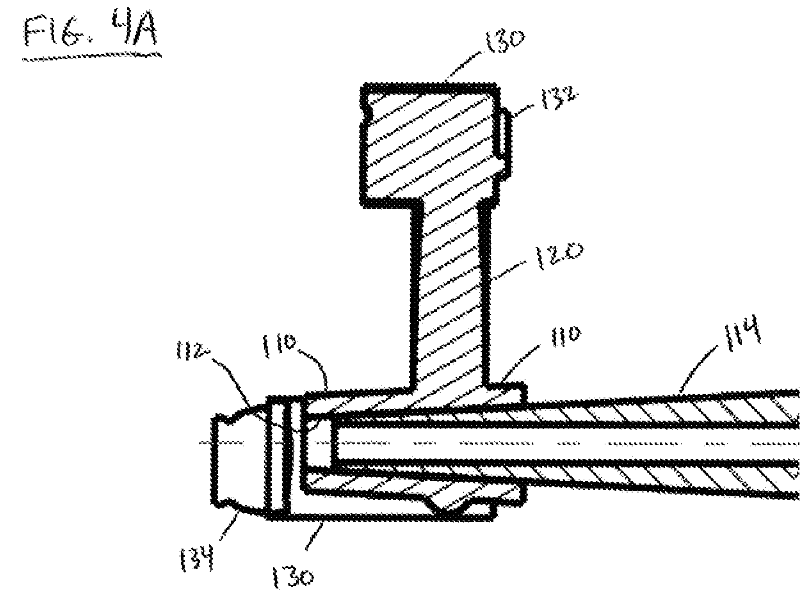
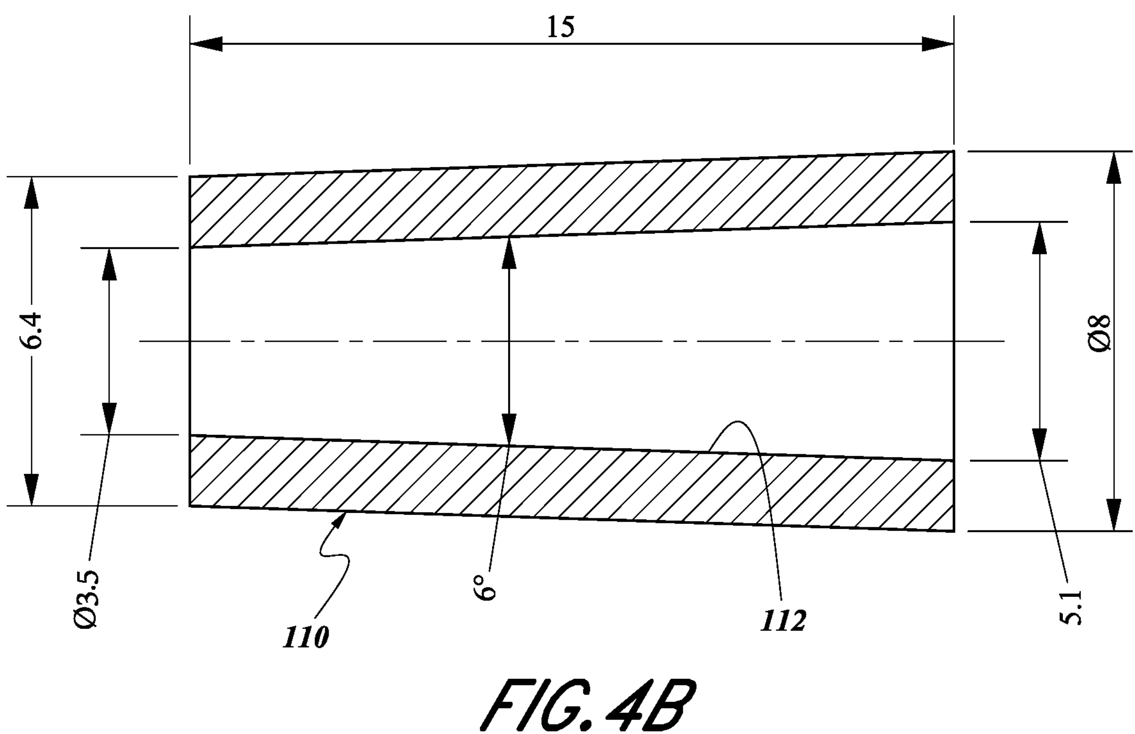
FIG. 4B 100
130
120
A
A
A
P
116
110

100

142
120
110
140
130
134

SHOULDER PATIENT SPECIFIC INSTRUMENT

CROSS-REFERENCE TO RELATED APPLICATIONS

The present application is a divisional of co-pending U.S. patent application Ser. No. 17,451,499, filed Oct. 20, 2021, which is a divisional of U.S. application Ser. No. 16/521,466, filed on Jul. 24, 2019, now U.S. Pat. No. 11,179,249, which is a divisional of U.S. application Ser. No. 15/024,747, filed on Mar. 24, 2016, now U.S. Pat. No. 10,405,993, which is a national phase of PCT International Application No. PCT/IB2014/002711, filed on Nov. 11, 2014, which claims priority benefit under 35 U.S.C. § 119(e) to U.S. Provisional Application No. 61/903,814, filed on Nov. 13, 2013, both of which are incorporated by reference in their entirety herein. Any and all applications for which a foreign or domestic priority claim is identified in the Application Data Sheet as filed with the present application are hereby incorporated by reference under 37 CFR 1.57.

BACKGROUND

Field of the Invention

The present invention relates to shoulder implants. In particular, the present invention relates to glenoid implants for shoulder joints having scapula erosion and devices that facilitate implanting the same.

Description of the Related Art

In a healthy shoulder joint, the head of the humerus interacts with the glenoid cavity of the scapula to form a "ball and socket" joint. The humeral head abuts and articulates with the glenoid to provide a wide range of motion. In an unhealthy shoulder joint, the interaction between the glenoid and the humerus is compromised, requiring repair or replacement.

Replacing the glenoid articular surface of the scapula of a human with a prosthetic glenoid component is a delicate surgical operation, notably because of the muscular environment of the shoulder. It is found that, depending on the position of implantation of such a glenoid component, risks of separation of the component from the underlying scapula exist due to forces applied to this component in subsequent movements of the prosthesized shoulder. In particular, in certain patients, it was found that, even if the implantation on their scapula of such a glenoid component was perfectly centered on the articular head of the corresponding humerus on completion of the surgical implantation operation, the resumption of their activities led, more or less rapidly, to instability of the prosthesis.

Currently, several companies are working on custom devices to guide glenoid bone preparation. One example filed by Tornier, Inc. is U.S. patent application Ser. No. 12/954,423, filed 24 Nov. 2010 and published as US 2011/0130795 A1.

SUMMARY

A patient specific glenoid guide is provided to facilitate properly aligned implantation of a glenoid prosthesis into a patient. The guide shape is designed preoperatively based on the unique configuration of the scapula of the patient. The guide orientation is chosen preoperatively based on one or more of the bone structure of the patient, the wear pattern of the patient's glenoid cavity, the anchoring means of the glenoid prosthesis, or other aspects.

The guide may reversibly snap into securement with the scapula of the patient to hold the guide to the scapula during surgery. The guide may establish one or more axes through the shoulder joint about which subsequent bone preparation procedures and prosthesis implantation may be carried out. The guide may allow insertion of one or more K-wires or pins through the guide and into the scapula along the axis, and also allow removal of the guide without removing the one or more K-wires or pins.

The patient specific glenoid guide may be comprised of a central tubular element and three or more peripheral arms emanating from the central tubular element. One or more arms may terminate in a peripheral peg. One or more peripheral peg may be configured to reversibly engage with the scapula of the patient. The guide may be made by rapid prototyping or three dimensional printing methods.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

BRIEF DESCRIPTION OF THE DRAWINGS

FIG. 4A illustrates a partial cross sectional side view of a patient specific glenoid guide.

FIG. 4B illustrates a cross sectional side view of a portion of a patient specific glenoid guide.

Figure 1:
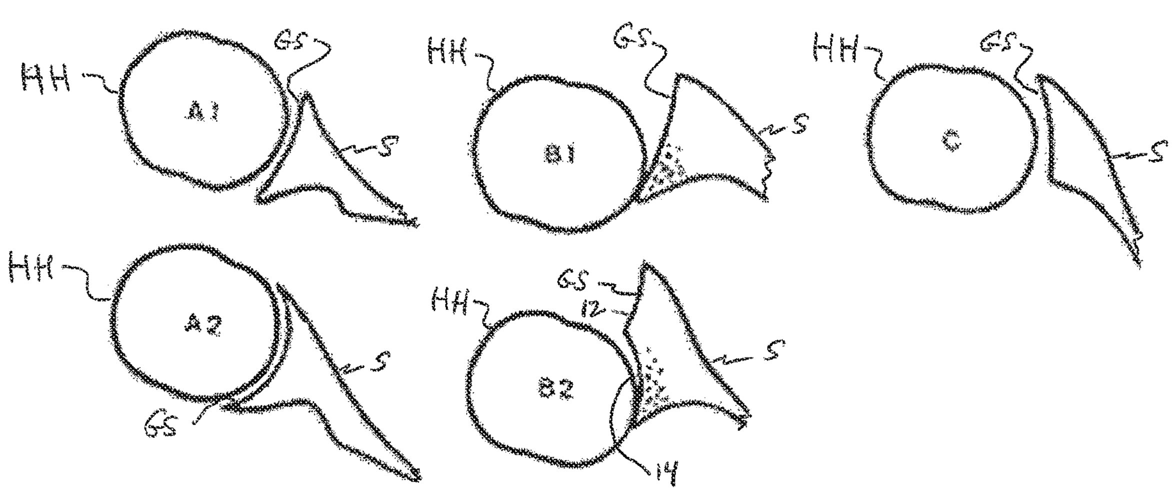
FIG. 1 illustrates schematic views of worn shoulder joints.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION OF THE PREFERRED EMBODIMENT

FIG. 1 illustrates five examples of worn shoulder joints that can be found in patients in need of shoulder arthroplasty. Each joint is comprised of a humeral head HH and a scapula S. The glenoid joint surface GS of the scapula is worn and can be classified as A1, A2, B1, B2, or C according to the shape of the glenoid surface ("Glenoid morphology in OA: Walch Classification", Walch G. et. al., J. Arthroplasty, 14:756-760, 1999). A glenoid GS may include a neo-glenoid portion 14 that has a significant amount of erosion and a paleo-glenoid portion 12 that has little or no erosion. Such a glenoid is commonly referred to as a "type-B2" glenoid (J. Bone Joint Surg. Br. 2011 vol. 93-B no. SUPP IV, 571). A prosthetic glenoid component (not shown) can be adapted to be positioned between the scapula and the humeral component. The glenoid component is also adapted to articulate with the humeral component. The humeral component may be a humeral prosthesis secured to the humerus of the subject or an anatomical humeral head of the subject.

As part of the process for restoring a functional articular surface to the scapula a glenoid implant is firmly attached to the scapula by a fixation means (not shown). In some examples the fixation means comprises one or more screws, pegs, keels, fins, cement, or other fixation means. It is desirable to establish proper orientation of the glenoid implant in relation to the scapula and the humerus to assure that the fixation means has adequate strength to resist implant dislodgement from forces generated by articular motions of the joint. For example, screws must have adequate pull-out strength to resist articular forces of the joint that tend to dislodge the implant from the shoulder bones. Further, proper orientation of the glenoid implant in relation to the scapula and the humerus can minimize the forces generated on the glenoid implant during articulation of the shoulder joint. To facilitate proper orientation of the glenoid implant an axis through the shoulder joint can be established and the axis used to properly orient the glenoid implant so as to accomplish the above goals.

Another part of the process for properly fitting a glenoid implant to the scapula can be preparing the worn surface of the scapula so that the prepared surface will match a previously prepared surface of the glenoid implant. A surgeon may need to remove a significant amount of bone including cortical bone of the relatively healthy portions of the glenoid to accommodate typical glenoid implants. When these matched surfaces are brought into apposition the combination will resist rocking, sliding, twisting, and other articular motions of the joint that tend to dislodge the implant from the shoulder bones. To facilitate proper orientation of the glenoid implant an axis through the shoulder joint can be established and the axis used to guide scapula surface preparation tools such as reamers, guides, broaches and other devices so as to accomplish the above goals.

Figures 2, 3:
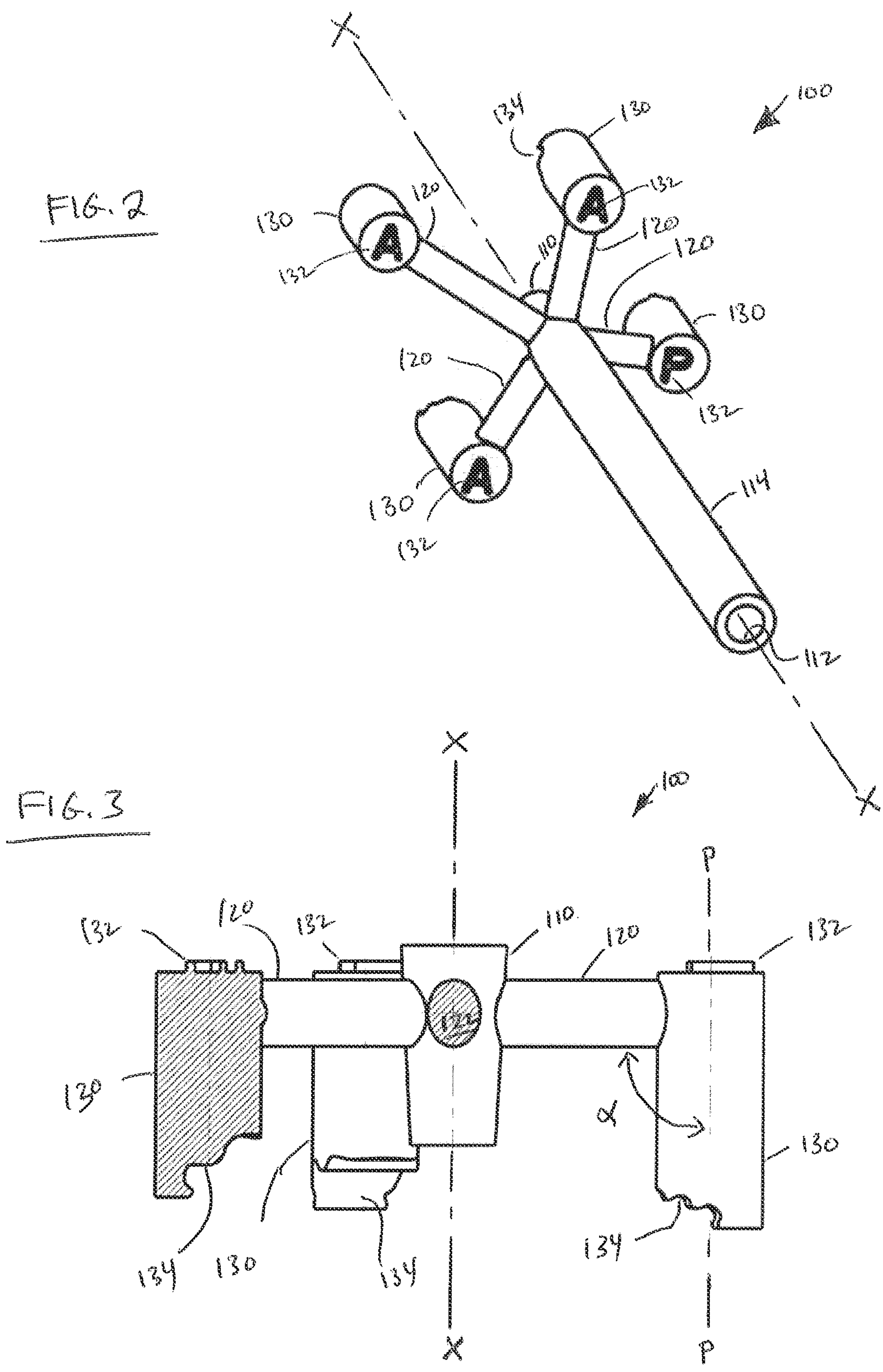
FIG. 2 illustrates an isometric plan view of a patient specific glenoid guide.
FIG. 3 illustrates a partial cross sectional side view of a patient specific glenoid guide.

FIGS. 2 and 3 illustrate one embodiment of a patient specific glenoid guide. Guide 100 is a unique structure based on the exact shoulder joint anatomy of a specific patient. Guide 100 is comprised of central tubular element 110, three or more arms 120, and at least three arms each having peripheral peg 130.

Central tubular element 110 is comprised of lumen 112 having axis X-X and is designed to guide a drill bit (not shown) for drilling a hole in the scapula. In another embodiment central tubular element 110 is designed to guide an alignment pin (not shown) through lumen 112 along axis X-X.

In a further embodiment (see FIGS. 4A and 4B) guide 100 is used with commercially available metallic pin guide 114 of a generic design that is not patient specific. Pin guide 114 can be engaged with lumen 112 of central tubular element 110 to hold the two components together during surgery. In one embodiment pin guide is engaged with central tubular element by friction fit. In another embodiment pin guide is engaged with central tubular element by locking conical tapers, in one example Morse tapers. Specific dimensions (in mm) of central tubular element 110 for one locking taper embodiment are illustrated in FIG. 4B, and pin guide 114 external mating dimensions are the same as the internal mating dimensions of the central tubular element. Typically pin guide 114 is long enough to function as a handle during surgery for placement of guide 100.

At least three arms 120 are provided on the guide, four arms are preferred, and 5, 6, 7, or 8 arms are contemplated. The arms between the central tubular element and each peripheral peg may have an elliptical, round, ovoid, polygonal, square, rectangular, triangular, other cross-section. In one embodiment the arm has an elliptical cross section and the major axis of the ellipse is perpendicular to the glenoid surface, the major axis is about 5 mm in length and the minor axis is about 4 mm in length. Arm 120 has a cross sectional area 122. Arm cross sectional areas of 10 square millimeters to 40 square millimeters and any cross sectional area therebetween are contemplated.

Peripheral peg 130 is comprised of identifier 132 and engagement surface 134. At least three pegs are provided on the guide, four pegs are preferred, and 5, 6, 7, or 8 pegs are contemplated. Three pegs are positioned to engage the anterior border of the glenoid cavity while one peg is positioned to engage the supero-posterior border of the glenoid cavity. Opposite to peg engagement surface 134, on the peg lateral extremity, the pegs are marked with identifier 132. In some embodiments anterior pegs are marked with identifier "A" while posterior pegs are marked with identifier "P". Peg diameters of 6 mm to 10 mm and any diameter therebetween are contemplated. In one embodiment peg diameter is 8 mm. In another embodiment the posterior peg axis P-P is angled at an obtuse angle $\alpha$ from the arm so as to not be in conflict with the posterior retractor during the arthroplasty procedure. Engagement surface 134 may be customized to closely conform to the 3 dimensional shape of the border of the glenoid cavity.

Figure 6:
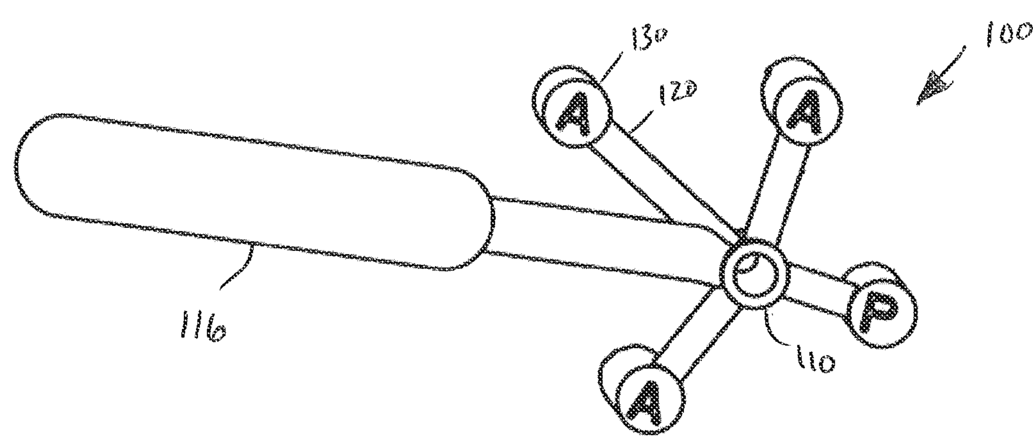
FIG. 6 illustrates an isometric plan view of an alternate embodiment of a patient specific glenoid guide.

Patient specific glenoid guide 100 optionally comprises handle 116 (FIG. 6). Handle 116 is long enough to function as a handle during surgery for placement of guide 100. Also, use of handle 116 instead of pin guide 114 for manipulation of guide 100 allows a short drill bit to be used through central tubular element 110 rather than a long drill bit through the combination of central tubular element 110 plus drill guide 114.

Figure 7:
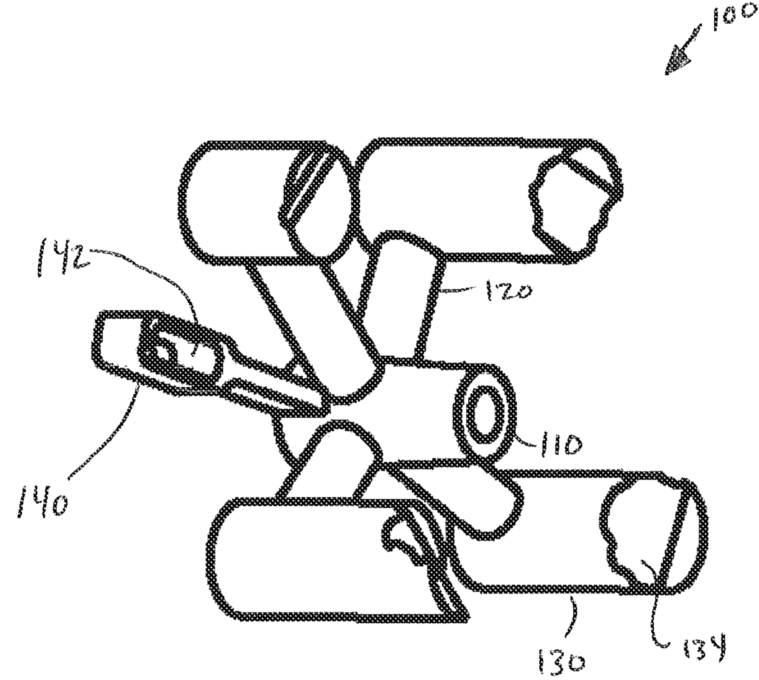
FIG. 7 illustrates an isometric bottom view of an alternate embodiment of a patient specific glenoid guide.

Patient specific glenoid guide 100 optionally comprises strut 140 having slot 142 (FIG. 7). The slot rotational position along the central axis X-X of the guide is the one of the supero-inferior axis of the glenoid component as determined by the pre-operative planning. Slot 142 is optionally used by the surgeon to mark this axis on the patient's bone with electrocautery.

In a further embodiment (not shown), second guide 100' is associated with first guide 100. Second guide 100' is similar to first guide 100 except that second guide 100' is designed to fit the patient's scapula after the scapula shape has been modified, for example, modified by reaming, and central tubular element 110' is comprised of two or more lumens 112', 112" having axes parallel to axis X-X. In some embodiment's lumens 112', 112" may be used to guide a drill bit (not shown) for drilling at least 2 holes in the scapula.

Guide 100 can be made by molding, machining, casting, thermal forming, or by other methods. In one embodiment guide 100 is made by rapid prototyping techniques, additive manufacturing or three dimensional printing using methods such as stereolithography or laser sintering. Guide 100 can be comprised of thermoplastics such as polyamide (such as PA2200 by Arptech) or metals such as titanium or stainless steel, or other materials.

Guide 100 is designed from three dimensional (3D) data about the anatomy of a patient's shoulder. The position and orientation of the axis X-X of the central tubular element 110 is defined according to pre-operative planning. The design process reproduces the translational positions of the glenoid component on three axes, (the antero-posterior axis, the supero-inferior axis and the medio-lateral axis) and it also reproduces the rotational positions of the glenoid component around the same three axes (supero-inferior axis (version), antero-posterior axis (inclination), and the medio-lateral axis (rotation)). By visualizing all of these positions a best choice position and orientation of axis X-X can be selected before operating on the patient. Also, a variety of glenoid implants can be evaluated for compatibility and performance in relation to the patients specific anatomy.

Figure 5:
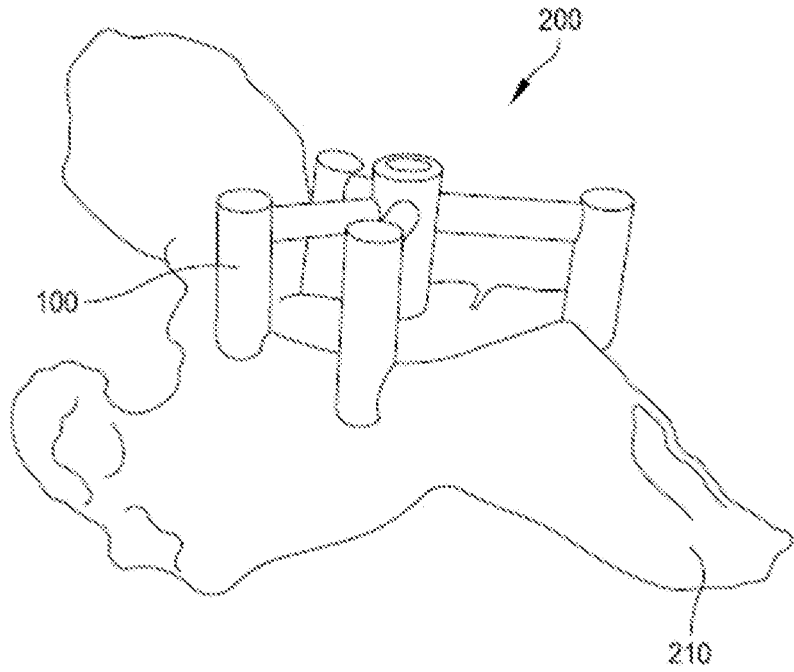
FIG. 5 illustrates an isometric plan view of a patient specific glenoid guide attached to a model of a patient's scapula.

In one exemplar embodiment a three dimensional model of the patients shoulder is generated from imaging data obtained using a medical imaging technique such as a CT scan or a MRI. The imaging data are processed manually or automatically to generate a 3D model of the patient's scapula. From the 3D model of the patient's scapula, patient-specific guide 100 is designed automatically or manually using various CAD programs and/or software available such as Solid Works or ProEngineer.

a. As a first step in this example the 3D model of the bone is displayed in a specific environment in which the surgeon is able to select the desired implant and to place it at the desired location and desired orientation in the 3D model of the patient's scapula. Alternatively the implant could be automatically selected and/or placed based on a set of pre-determined criteria such as those described in EP2324801A1 or US2011/0119884 A1 which are incorporated herein in their entirety and can be found in the Appendix.
b. As a second step in this example, once the implant is selected and placed in position in the 3D model of the patient's scapula the location of the pegs is determined by the surgeon or by an engineer. Then the guide structure, including central tubular element 110, arms 120, pegs 130, and all of their features as described above, is manually or automatically generated. A dilatation of 2 pixels of the outside dimensions of the scapula is applied to bone model, and therefore to the guide engagement surface, in order to get a proper fit between the guide and the bone model as well as between the guide and the native bone.
c. The patient-specific guide 100 so generated will have a three dimensional engagement surface at the distal end of each peg that is complementary and made to conformingly contact the anatomical surface of the glenoid cavity border. The patient-specific guide 100 is thereby configured to fit at a unique position to the anatomical surface of the scapula. The central element of the guide so generated is in the proper location and orientation for proper location of the glenoid implant.
d. Optionally a 3D bone model 210 of the patient's scapula can be produced from the 3D imaging data, and said model can be provided to the surgeon with guide 100 as part of an implant kit 200 (FIG. 5). Such a model will allow the surgeon to test the fit and orientation of the guide 100 against the model of the patient's scapula prior to surgery, and can be a reference for the surgeon during surgery.

A non-limiting exemplar method of use of the patient specific glenoid guide is now described.

a. A patient undergoes a medical imaging technique such as a CT scan or a MRI and the imaging datum are processed manually or automatically to generate a 3D model of the patient's scapula.
b. The 3D model of the scapula is displayed in a specific environment in which the surgeon selects the desired implant and places it at the desired location and desired orientation in the 3D model of the patient's scapula. Alternatively the implant is automatically selected and/or placed based on a set of pre-determined criteria such as those described in EP2324801A1 or US2011/0119884 A1 which are incorporated herein in their entirety and can be found in the Appendix.
c. The location of 4 pegs is determined by the surgeon or by an engineer.
d. The guide structure, including central tubular element 110, arms 120, pegs 130, and all of their features as described above, is manually or automatically generated. A dilatation of 2 pixels of the outside dimensions of the scapula is applied to bone model, and therefore to the guide engagement surface, in order to get a proper fit between the guide and the bone model as well as between the guide and the native bone.
e. Optionally a 3D bone model of the patient's scapula is produced from the 3D imaging data.
f. The glenoid guide is provided to the surgeon. Optionally, a kit comprised of the 3D bone model and glenoid guide is provided to the surgeon.
g. The surgeon exposes the glenoid cavity of the patient.
h. The glenoid guide is pressed onto the border of the glenoid cavity and engages the glenoid in a snap fit attachment.
i. Pin placement through lumen 112 of guide 110 into patients scapula is performed.
j. Guide 110 is removed from the pin.
k. Scapula surface preparation and/or glenoid prosthesis placement is performed using pin as a guide.
l. Pin is removed.
m. Remainder of shoulder arthroplasty procedure is completed.

Terminology

Conditional language, such as "can," "could," "might," or "may," unless specifically stated otherwise, or otherwise understood within the context as used, is generally intended to convey that certain embodiments include, while other embodiments do not include, certain features, elements, and/or steps. Thus, such conditional language is not generally intended to imply that features, elements, and/or steps are in any way required for one or more embodiments.

The term "about" as used herein represent an amount close to the stated amount that still performs a desired function or achieves a desired result. For example, the term "about" may refer to an amount that is within less than 10% of the stated amount, as the context may dictate.

Any methods disclosed herein need not be performed in the order recited. The methods disclosed herein include certain actions taken by a practitioner; however, they can also include any third-party instruction of those actions, either expressly or by implication. For example, actions such as "positioning three pegs around an anterior anatomical feature adjacent of the a glenoid cavity" include "instructing the positioning of three pegs around an anterior anatomical feature adjacent of the a glenoid cavity."

Although certain embodiments and examples have been described herein, it will be understood by those skilled in the art that many aspects of the glenoid guide shown and described in the present disclosure may be differently combined and/or modified to form still further embodiments or acceptable examples. All such modifications and variations are intended to be included herein within the scope of this disclosure. A wide variety of designs and approaches are possible. No feature, structure, or step disclosed herein is essential or indispensable.

Some embodiments have been described in connection with the accompanying drawings. However, it should be understood that the figures are not drawn to scale. Distances, angles, etc. are merely illustrative and do not necessarily bear an exact relationship to actual dimensions and layout of the devices illustrated. Components can be added, removed, and/or rearranged. Further, the disclosure herein of any particular feature, aspect, method, property, characteristic, quality, attribute, element, or the like in connection with various embodiments can be used in all other embodiments set forth herein. Additionally, it will be recognized that any methods described herein may be practiced using any device suitable for performing the recited steps.

For purposes of this disclosure, certain aspects, advantages, and novel features are described herein. It is to be understood that not necessarily all such advantages may be achieved in accordance with any particular embodiment. Thus, for example, those skilled in the art will recognize that the disclosure may be embodied or carried out in a manner that achieves one advantage or a group of advantages as taught herein without necessarily achieving other advantages as may be taught or suggested herein.

Moreover, while illustrative embodiments have been described herein, the scope of any and all embodiments having equivalent elements, modifications, omissions, combinations (e.g., of aspects across various embodiments), adaptations and/or alterations as would be appreciated by those in the art based on the present disclosure. The limitations in the claims are to be interpreted broadly based on the language employed in the claims and not limited to the examples described in the present specification or during the prosecution of the application, which examples are to be construed as non-exclusive. Further, the actions of the disclosed processes and methods may be modified in any manner, including by reordering actions and/or inserting additional actions and/or deleting actions. It is intended, therefore, that the specification and examples be considered as illustrative only, with a true scope and spirit being indicated by the claims and their full scope of equivalents.

EXAMPLE EMBODIMENTS

The following example embodiments identify some possible permutations of combinations of features disclosed herein, although other permutations of combinations of features are also possible.

1. A patient specific glenoid guide for attachment to a scapula of a patient, the glenoid guide comprising:
   a guide feature;
   at least three arms having a first end coupled with the guide feature and a second end disposed away from the guide feature; and
   at least three peripheral pegs, each peripheral peg extending from the second end of a corresponding arm and comprising an engagement surface;
   wherein the engagement surface is configured to engage the scapula of the patient to provide a snap fit attachment onto the scapula.
2. The patient specific glenoid guide of Embodiment 1, wherein the guide feature comprises a central tubular element that comprises a lumen.
3. The patient specific glenoid guide of Embodiment 1 or 2, wherein the guide feature is tapered.

4. The patient specific glenoid guide of any one of Embodiments 1 to 3, wherein the guide feature is configured to receive a pin guide.
5. The patient specific glenoid guide of any one of Embodiments 1 to 4, wherein the at least three peripheral pegs comprises four peripheral pegs.
6. The patient specific glenoid guide of Embodiment 5, wherein three of the four peripheral pegs are configured to engage an anterior anatomical feature of the scapula, and wherein one of the four peripheral pegs is configured to engage a supero-posterior anatomical feature of the scapula.
7. The patient specific glenoid guide of Embodiment 6, wherein three of the four peripheral pegs are configured to engage an anterior border of a glenoid cavity, and wherein one of the four peripheral pegs is configured to engage a supero-posterior border of the glenoid cavity.
8. The patient specific glenoid guide of any one of Embodiments 1 to 7, wherein each of the at least three arms comprises an elliptical cross section, the major axis of the elliptical cross-section being perpendicular to a glenoid cavity when the glenoid guide is coupled with the scapula.
9. The patient specific glenoid guide of any one of Embodiments 1 to 8, wherein an angle between one of the at least three arms and a corresponding peg is an obtuse angle.
10. The patient specific glenoid guide of any one of Embodiments 1 to 9, further comprising a lateral handle extending laterally from the guide feature.
11. The patient specific glenoid guide of any one of Embodiments 1 to 10, further comprising a strut extending laterally from the guide feature, the strut comprising a slot.
12. A system for guiding a glenoid prosthesis, the system comprising:
    the glenoid guide of any one of Embodiments 1 to 11; and
    a pin guide configured to engage the guide feature.
13. The system of Embodiment 12, wherein the pin guide comprises a tapered surface, and wherein the guide feature is tapered to receive the tapered pin guide.
14. A surgical kit comprising:
    a patient specific glenoid guide, the glenoid guide comprising:
    a guide feature;
    a plurality of arms extending from the guide feature; and
    a plurality of peripheral pegs, each of the plurality of peripheral pegs extending from a corresponding arm, each of the plurality of peripheral pegs comprising an engagement surface; and
    a three dimensional model of a patient's scapula comprising a glenoid cavity border; and
    wherein the engagement surfaces of the patient specific glenoid guide are configured to engage the glenoid cavity border of the model by a snap fit.
15. The surgical kit of Embodiment 14, wherein the guide feature comprises a central tubular element that comprises a lumen.
16. The surgical kit of Embodiment 14 or 15, wherein the guide feature is tapered.
17. The surgical kit of any one of Embodiments 14 to 16, wherein the guide feature is configured to receive a pin guide.

18. The surgical kit of any one of Embodiments 14 to 17, wherein the plurality of peripheral pegs comprises four peripheral pegs.
19. The surgical kit of Embodiment 18, wherein three of the four peripheral pegs are configured to engage an anterior portion of the glenoid cavity border, and wherein one of the four peripheral pegs is configured to engage a supero-posterior portion of the glenoid cavity border.
20. The surgical kit of any one of Embodiments 14 to 19, wherein each of the plurality of arms comprises an elliptical cross section, the major axis of the elliptical cross-section being perpendicular to a portion of the model corresponding to a glenoid cavity when the guide is applied to the model.
21. The surgical kit of any one of Embodiments 14 to 20, wherein an angle between one of the plurality of peripheral pegs and the corresponding arms is an obtuse angle.
22. The surgical kit of any one of Embodiments 14 to 21, further comprising a lateral handle extending laterally from the guide feature.
23. The surgical kit of any one of Embodiments 14 to 22, further comprising a strut extending laterally from the guide feature, the strut comprising a slot.
24. The surgical kit of any one of Embodiments 14 to 23, further comprising a pin guide coupled to the guide feature.
25. A method of guiding a glenoid prosthesis, the method comprising:
    - pre-operatively determining a position and an orientation of guide feature of a glenoid guide based on a specific patient's scapula, the glenoid guide comprising:
    - a plurality of arms extending from the guide feature; and
    - a peripheral peg extending from each of the plurality of arms, the guide feature disposed inward of the peripheral pegs;
    - engaging the glenoid guide with the scapula;
    - inserting a pin having an axis through the guide feature to or through the scapula.
26. The method of Embodiment 25, wherein the guide feature comprises a central tubular element that comprises a lumen and inserting the pin comprises inserting the pin through the lumen of the guide feature.
27. The method of Embodiment 25 or 26, wherein engaging the glenoid guide with the scapula comprises engaging the glenoid guide with a glenoid cavity border by snap fit.
28. The method of any one of Embodiments 25 to 27, wherein engaging the glenoid guide with the scapula comprises positioning three pegs around an anterior anatomical feature of a glenoid cavity and positioning one peg at a supero-posterior anatomical feature of the glenoid cavity.
29. The method of Embodiment 28, wherein engaging the glenoid guide with the scapula comprises positioning three pegs around an anterior anatomical border of the glenoid cavity and positioning one peg at a supero-posterior border of the glenoid cavity.
30. The method of any one of Embodiments 25 to 29, further comprising advancing the glenoid prosthesis along the pin.
31. The method of any one of Embodiments 25 to 30, further comprising securing the pin to the guide feature by a friction fit.
32. The method of any one of Embodiments 25 to 30, further comprising securing a conical taper of the pin with a conical taper of the guide feature.

What is claimed is:

1. A system for guiding a glenoid prosthesis that includes a glenoid component, the system comprising:

a glenoid guide that comprises:

a central tubular element defining a lumen;

at least three arms radially extending from the central tubular element, each arm of the at least three arms having a first end coupled with the central tubular element and a second end disposed away from the central tubular element;

at least three peripheral pegs, each peripheral peg extending from the second end of a corresponding arm, extending away from a bone-facing surface of the corresponding arm, and comprising an engagement surface configured to engage a peripheral border of a glenoid cavity of a patient; and a strut radially extending from the central tubular element, the strut comprising a positioning opening; and a pin guide configured to be at least partially received within the lumen defined by the central tubular element, wherein a longitudinal direction of each of the at least three peripheral pegs extends substantially orthogonally from an axis defined by the corresponding arm of the at least three arms such that each arm of the at least three arms is spaced apart from a glenoid when each engagement surface of the at least three peripheral pegs engages the peripheral border of the glenoid cavity.

2. The system of claim 1, wherein the central tubular element comprises a tapered surface configured to engage a corresponding tapered surface of the pin guide.

3. The system of claim 1, wherein the positioning opening is provided to be positioned along a supero-inferior axis of the glenoid component when the glenoid guide is being used to guide the glenoid component with respect to the glenoid cavity of the patient.

4. The system of claim 1, wherein a position and orientation of the central tubular element is provided to control a translational and rotational position of the glenoid component during implantation.

5. The system of claim 4, wherein the position and orientation of the central tubular element provides translational control along an axis.

6. The system of claim 1, wherein the central tubular element is configured so that one or more pins are insertable through the glenoid guide to establish one or more axes about which subsequent bone preparation procedures can be carried out.

7. The system of claim 1, wherein the glenoid guide comprises two or more lumens having parallel axes.

8. The system of claim 1, wherein the at least three peripheral pegs comprises four peripheral pegs.

9. The system of claim 8, wherein three peripheral pegs of the four peripheral pegs are positioned to engage an anterior border of the glenoid cavity and a fourth peripheral peg of the four peripheral pegs is positioned to engage a supero-posterior border of the glenoid cavity.

10. The system of claim 1, wherein the at least three peripheral pegs have a cross-section that is round.

11. A system for guiding a glenoid prosthesis that includes a glenoid component, the system comprising:

a glenoid guide, including:

a central tubular element defining a lumen configured to receive a pin guide;

a plurality of arms, each arm having a first end coupled with central tubular element and a second end disposed away from the guide feature such that each arm of the plurality of arms extends radially outwardly from the guide feature; and a plurality of peripheral pegs having a circular cross-section, wherein each peripheral peg includes a lateral end being coupled to the second end of a corresponding one of the plurality of arms, the peripheral peg extending away from a bone-facing surface of the corresponding arm, and comprising an engagement surface at a medial end, the engagement surface configured to conform to a three dimensional shape of a glenoid cavity border of a scapula of a patient such that each arm of the plurality of arms is spaced apart from a lateral surface of a glenoid when each of the engagement surfaces contacts the border of the glenoid cavity, wherein a longitudinal direction of each of the plurality peripheral pegs extends substantially orthogonally from an axis defined by the corresponding arm of the plurality of arms such that each arm of the plurality of arms is spaced apart from a glenoid when each engagement surface of the plurality of peripheral pegs engages the glenoid cavity border of the scapula.

* * * * *